United States Patent [19]
Wolff

[11] 4,177,384
[45] * Dec. 4, 1979

[54] APPARATUS FOR PRODUCING ULTRAVIOLET RADIATION

[76] Inventor: Friedrich Wolff, Lindenring 17, D-6000 Frankfurt am Main, Fed. Rep. of Germany

[ * ] Notice: The portion of the term of this patent subsequent to Jun. 13, 1995, has been disclaimed.

[21] Appl. No.: 880,567

[22] Filed: Feb. 23, 1978

Related U.S. Application Data

[63] Continuation-in-part of Ser. No. 716,253, Aug. 20, 1976, Pat. No. 4,095,113, and Ser. No. 716,254, Aug. 20, 1976, Pat. No. 4,106,083.

[30] Foreign Application Priority Data

Feb. 24, 1977 [DE] Fed. Rep. of Germany ....... 2707920

[51] Int. Cl.$^2$ .................................................. G01J 1/00
[52] U.S. Cl. .................................. 250/494; 250/504; 250/510
[58] Field of Search ............... 250/503, 504, 510, 455, 250/451, 494; 128/371, 372, 373; 313/484, 489; 362/217

[56] References Cited
U.S. PATENT DOCUMENTS

| | | | |
|---|---|---|---|
| 1,739,509 | 12/1929 | Goodrich | 250/454 |
| 1,786,205 | 12/1930 | Greider | 250/504 |
| 2,273,449 | 2/1942 | Plishker | 250/494 |
| 3,160,755 | 12/1964 | Wolfe | 250/503 |
| 4,003,704 | 1/1977 | Zurolo et al. | 250/455 |
| 4,055,769 | 10/1977 | Sander | 250/504 |
| 4,095,113 | 6/1978 | Wolff | 250/494 |

*Primary Examiner*—Bruce C. Anderson
*Attorney, Agent, or Firm*—Peter K. Kontler

[57] ABSTRACT

Apparatus for treatment of psoriasis has a housing with an exit opening located in front of a battery of elongated cylindrical low-pressure mercury lamps which emit ultraviolet radiation in the UVB and UVA ranges, with abrupt decrease of radiation intensity at the wavelength of approximately 330 nm. The envelopes of the lamps absorb radiation in the wavelength band below approximatey 295 nm. Each lamp is partially surrounded by a trough-shaped reflector which reflects radiation issuing from the rear half and from the sides of the respective lamp. The reflectors cause the radiation to form a high-intensity radiation field close to the exit opening of the housing. If the exit opening is located above the lamps, it is covered by a plate which transmits radiation between 300 and 330 nm and serves as a support for the body of a patient. A similar apparatus can be installed above the support, and a third apparatus can be installed laterally of the other two apparatus so as to enable a patient to expose three sides of his or her body to ultraviolet radiation in the wavelength band between 300 and 330 nm.

15 Claims, 8 Drawing Figures

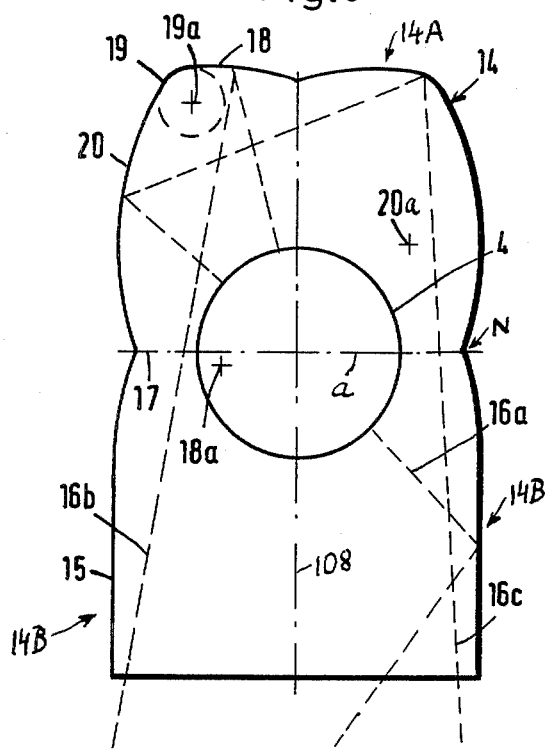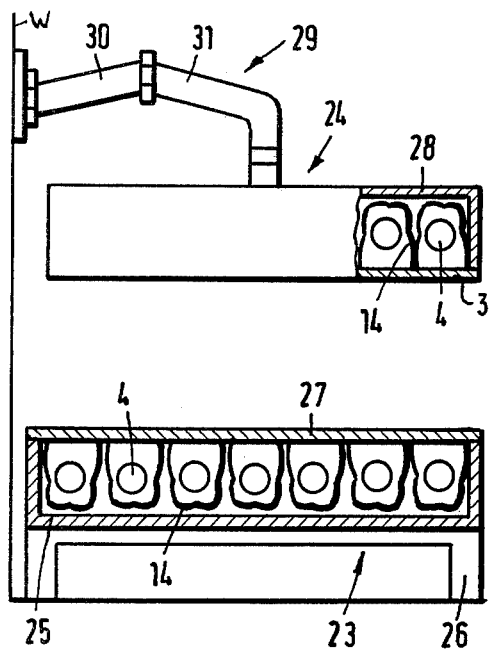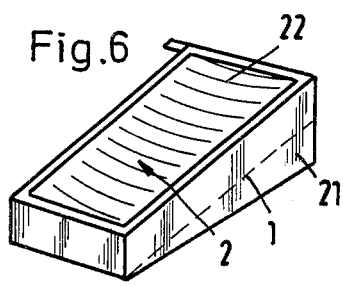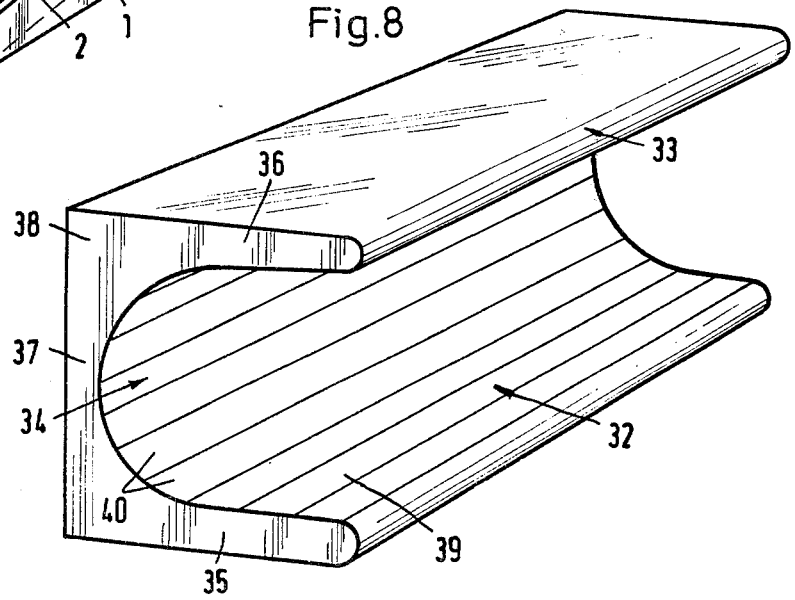

APPARATUS FOR PRODUCING ULTRAVIOLET RADIATION

CROSS-REFERENCE TO RELATED CASES

This is a continuation-in-part of my copending patent applications Ser. Nos. 716,253 and 716,254 both filed Aug. 20, 1976, now U.S. Pat. Nos. 4,095,113 and 4,106,083 granted June 13 and Aug. 8, 1978, respectively. The disclosures of my aforesaid copending applications are incorporated herein by reference.

BACKGROUND OF THE INVENTION

The present invention relates to apparatus for producing ultraviolet radiation, especially for treatment of psoriasis and certain other skin diseases.

It is known to treat psoriasis and similar skin diseases by exposing the affected area of the skin to a narrow range (approximately 300–330 nm) of ultraviolet radiation, namely, to radiation in the upper portion of the so-called UVB range ("Dorno" region of 280 to 315 nm) and in the lower portion of the so-called UVA range ("near" region of 315 to 400 nm). The aforementioned spectral zone between approximately 300 and 330 nm includes radiation which contains sufficient amounts of quantum energy for the skin treatment and is capable of penetrating into the epidermis to reach the inner boundary of the epidermis, i.e., the stratum which is the staging point of psoriasis. The just discussed spectral zone is immediately adjacent to that portion of the UVB range which causes sunburn; therefore, the lower limit of the desirable spectral zone for treatment of psoriasis or related diseases must be selected and maintained with a high degree of accuracy. The quantum energy of radiation in the spectral region above approximately 330 nm is too low to exert any beneficial antipsoriatic effect.

A presently known apparatus for treatment of psoriasis employs a source of ultraviolet radiation which comprises a high-pressure metal vapor lamp whose contents are selected in such a way that the radiation includes several pronounced spectral lines in the region between 300 and 330 nm. The lamp is a point source of radiation and, therefore, such lamp cannot insure uniform irradiation of large areas, e.g., of the major part of or the entire body of a patient. Moreover, the emission of light and heat energy is so high that the source must be held at a considerable distance from the patient, i.e., the density of the radiation field in the region of the affected area is low so that the patient must be exposed to radiation for extended periods of time. Another drawback of conventional apparatus is that they also emit radiation in several narrow zones of the lower ultraviolet range of the spectrum.

OBJECTS AND SUMMARY OF THE INVENTION

An object of the invention is to provide an apparatus for treatment of certain skin diseases which is constructed and assembled in such a way that it can establish a large-area high-density radiation field without causing sunburn or other undesirable side effects.

Another object of the invention is to provide an apparatus which can be used in hospitals, doctors' offices, nursing homes, public places or in private homes as a superior substitute for presently known apparatus which treat psoriasis and related skin diseases by exposure to ultraviolet radiation.

A further object of the invention is to provide an apparatus which is sufficiently simple and safe to warrant its use by patients without any supervision by or assistance from physicians, nurses or other skilled persons.

An additional object of the invention is to provide an apparatus which can subject large areas of the skin or the entire body of a patient to a high-density radiation field while the patient can assume a position which is sufficiently comfortable to enable the patient to stand the treatment for any desired period of time.

The invention is embodied in an apparatus for selective treatment with ultraviolet radiation, especially for treatment of skin diseases including psoriasis. The apparatus comprises a housing having an exit opening and containing a plurality (preferably between 5 and 20, most preferably between 10 and 12) of closely adjacent parallel elongated sources of ultraviolet radiation (preferably low-pressure mercury lamps) which emit a continuous spectrum of ultraviolet radiation whose intensity is highly pronounced in the lower part and decreases rather abruptly in the upper part of the UVA range, and filter means (such filter means may constitute glass envelopes of the mercury lamps) for absorbing radiation in and below the region between the UVB and UVA ranges. The intensity of radiation preferably decreases at the wavelength of approximately 330 nm, and the filter means preferably absorbs radiation in the wavelength band below approximately 295 nm.

The spacing between neighboring radiation sources is preferably less than and preferably does not exceed the diameter of the envelope of a radiation source.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTON OF THE DRAWING

FIG. 5 is a schematic cross-sectional view of a radiation source and of a modified trough-shaped reflector which is associated with the radiation source;

FIG. 6 is a perspective view of an apparatus with a battery of substantially horizontal radiation sources and a plate-like cover which constitutes a support for the body of a patient;

FIG. 7 is a partly elevational and partly sectional view of a third apparatus with two batteries of radiation sources located one above the other; and FIG. 8 is a perspective view of a fourth apparatus with three batteries of radiation sources.

DESCRIPTION OF THE PREFERRED EMBODIMENTS

Figure 1:
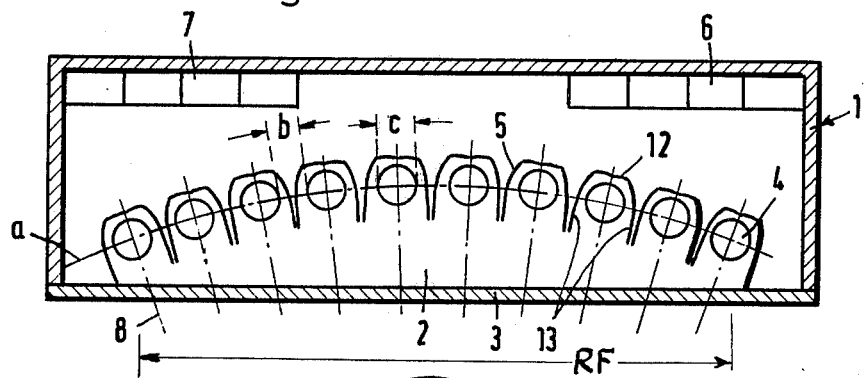
FIG. 1 is a horizontal sectional view of an apparatus with a battery of ten upright radiation sources which embodies one form of the invention.

The apparatus of FIG. 1 comprises a housing 1 having a front side with an exit opening or window 2 for ultraviolet radiation. The window 2 contains a glass pane 3 which transmits radiation at least in the range between approximately 300 and 330 nm. The housing 1 contains a battery of ten parallel upright rod-shaped radiation sources 4 each of which is a low-pressure mercury lamp. The neighboring lamps 4 are equally spaced from each other and the axes of all lamps are located in a slightly arcuate plane a. Each lamp 4 is associated with a trough-shaped reflector 5 which surrounds the respective lamp along an arc of at least 180 degrees. The housing 1 further contains auxiliary equipment 6 (e.g., timers and chokes) for the lamps 4 and controls 7 which can be actuated by one or more knobs, not shown.

The distance b between two neighboring lamps 4 is less than (preferably approximately 70 percent of) the diameter c of a lamp. Thus, the distance between the central symmetry planes 8 of two neighboring lamps 4 (as measured in the arcuate plane a) equals b+c. The planes 8 are normal to the adjacent portions of the arcuate plane a. The length of each lamp 4 is approximately 150 cm. The area of the high-density radiation field RF immediately in front of the glass pane 3 is approximately 70 by 150 cm. This area can be varied by changing the number and/or length of the lamps 4.

The reflectors 5 of FIG. 1 resemble one of the reflectors which are shown and described in my copending application Ser. No. 716,254 filed Aug. 20, 1976 for "Reflector for use in sunlamps or the like" now U.S. Pat. No. 4,106,083. Each reflector 5 has a curved rear wall 12 with a centrally located notch which is closely adjacent to the respective lamp 4, and two partially curved side walls 13 which extend forwardly beyond the respective lamp. The edges between the rear wall 12 and the side walls 13 may but need not be pronounced. The distance between the side walls 13 increases gradually in the rear half of the reflector 5, i.e., between the rear wall 12 and the plane a, and thereupon remains substantially constant. The width of the open front side of the reflector 5 (between the front edges of the side walls 13) is slightly less than b+c. The extent to which the side walls 13 project forwardly beyond the respective lamp 4 can exceed the radius of the lamp.

The number of lamps 4 may vary. The minimum number should not be less than five, and the maximum number need not exceed twenty. The presently preferred number is between ten and twelve lamps. Each of these lamps resembles an elongated rod-like fluorescent lamp, and each lamp emits a continuous spectrum of ultraviolet radiation.

An advantage of the improved apparatus is that it produces a large-area high-density radiation field which insures rapid results and can cover a large part of a human body. The effect of radiation is uniform in all parts of the field, and the radiation is most effective in that wavelength band of ultraviolet light whose effects upon the diseased skin are highly beneficial. The envelopes 9 of the lamps protect the patient from sunburn. Moreover, and since the generation of light and/or heat is negligible or nil, the apparatus remains cold and thus enables the patient to undergo a treatment of desired duration. The space requirements of the apparatus are surprisingly low because the high-density radiation field is or can be located in immediate or close proximity of the exit opening.

Figure 2:
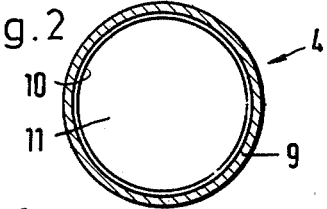
FIG. 2 is an enlarged transverse cross-sectional view of a radiation source.
Figure 3:
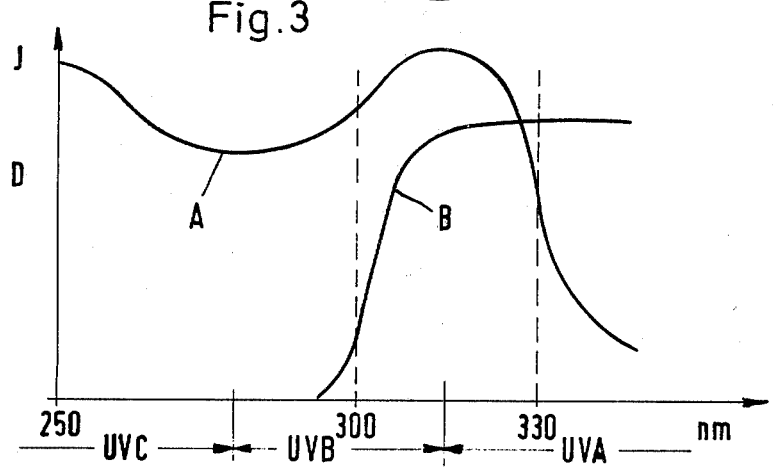
FIG. 3 is a diagram whose curves denote the intensity of emitted radiation in different wavelength bands of the spectrum and the transmissivity of the filter means.
Figure 4:
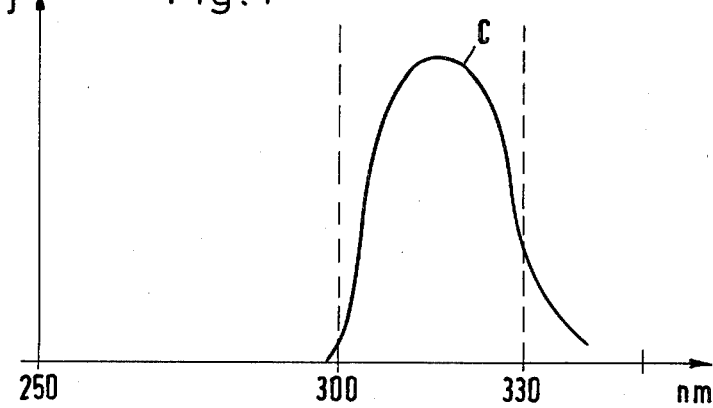
FIG. 4 is a diagram whose curve denotes the intensity of radiation furnished by the apparatus of FIG. 1.

FIG. 2 shows one of the lamps 4. The cylindrical glass envelope or shell 9 of the lamp constitutes a filter for radiation and its inner side is coated with a layer 10 of luminous material. The internal space 11 of the lamp 4 is filled with mercury vapors and such space further contains electrodes and other components of a low-pressure mercury lamp. The luminous layer 10 converts the spectral lines issuing from mercury vapors into a continuous spectrum. The material of the layer 10 is selected in such a way that the intensity of radiation is especially pronounced in the region between 300 and 330 nm and decreases abruptly at the upper limit of such region. This is represented by the curve A in the diagram of FIG. 3 wherein the intensity of radiation (J) is plotted against the wavelength (in nm). For example, the layer 10 can contain cerium-activated strontium aluminate and preferably traces of substances which cause radiation above 330 nm. The transmissivity D of the envelope 9 is represented by the curve B of FIG. 3. The material of the envelope 9 absorbs radiation below approximately 295 nm and its transmissivity rises abruptly above such wavelength. For example, the envelope 9 may be made of natron-calcium glass which contains minute traces of iron. The combination of the layer 10 and envelope 9 enables the lamp 4 to emit radiation in the wavelength band between 300 and 330 nm as represented by the curve C of FIG. 4 wherein the intensity J is plotted against wavelength (in nm). Thus, each lamp 4 furnishes radiation which is confined, almost exclusively, to the desirable band between 300 and 330 nm. The band UVC denotes in FIG. 3 the so-called "far" region of the spectrum.

The generation of a uniform high-density radiation field is enhanced by placing the neighboring lamps 4 close to each other. The spacing between neighboring lamps need not exceed the radius of a lamp and should not exceed the diameter of a lamp.

The utilization of lamps whose envelopes constitute radiation filters contributes to compactness and lower cost of the apparatus. Such envelopes replace discrete filters which are used in many conventional sunlamps between the radiation source and the exit opening. Consequently, the lamps 4 can be placed in close proximity of the exit opening 2.

FIG. 5 illustrates a modified trough-shaped reflector 14 which can be used as a substitute for the reflectors 5 of FIG. 1. The reflector 14 is similar to one of the reflectors which are shown in my aforementioned copending application Ser. No. 716,254. This reflector comprises a rear wall 14A and two side walls 14B which are mirror symmetrical to each other with reference to the corresponding central symmetry plane 108. The front portions 15 of the side walls 14B are parallel to each other and extend forwardly beyond the lamp 4. The rear portions 20 of the side walls 14B are curved and define with the front portions 15 pronounced notches N in the plane a. The purpose of the front portions 15 is to reflect rays, such as the ray 16a, which impinge upon their inner sides so that all rays issuing from the lamp 4 (either directly through the front side of the reflector 14 or upon reflection as a result of impingement on the rear or side walls) form a bundle which travels in the desired direction, i.e., to form part of the high-density radiation field RF shown in FIG. 1. The rear wall 14A comprises two mirror symmetrical arcuate halves 18 and is connected with the rear portions 20 of the side walls 14B by two arcuate intermediate walls 19. The illustrated configuration of the rear wall 14A, the intermediate walls 19 and rear portions 20 of side walls 14B insures that the major percentage of rays (such as 16b and 16c) which issue from the rear half of the lamp 4 is deflected forwardly through the relatively narrow clearances or gaps 17 between the notches N and the nearest portions of the lamp 4. This insures that the rays issuing from the rear side of the lamp 4 undergo a negligible damping action and that radiation losses (save for losses due to reflection) are extremely low. The center of curvature of the left-hand half 18 of the rear wall 14A is shown at 18a, the center of curvature of the left-hand rear portion 20 is shown at 20a, and the center of curvature of the left-hand intermediate wall 19 is shown at 19a. The left-hand half 18 of the rear wall 14A reflects the ray 16b into the left-hand gap 17, and the right-hand intermediate wall 19 reflects the ray 16c into the right-hand gap 17. The curvature of the intermediate walls 19 is much more pronounced than that of the halves 18 and rear portions 20. The curvature of each rear portion 20 may equal or approximate the curvature of each half 18. It will be noted that the ray 16c is reflected first by the left-hand rear portion 20 and thereupon by the right-hand intermediate wall 19 before it passes through the right-hand gap 17. The configuration of the reflector 14 contributes significantly to density of the radiation field immediately in front of the exit opening of the housing.

The trough-shaped reflectors (5 or 14) invariably insure that the rays which issue from the respective radiation sources are directed forwardly toward the exit opening in spite of the fact that the radiation sources are closely adjacent to each other. The front portions of the side walls of neighboring reflectors are preferably placed in immediate proximity of each other. Such front portions can be secured to each other, for example, in a manner as disclosed in the copending application Ser. No. 716,254. Since the front portions extend well beyond the foremost portion of the respective radiation source, the percentage of stray radiation is negligible.

FIG. 6 shows an apparatus wherein the housing 1 rests on a wedge-like base 21. Alternatively, the entire housing 1 can be installed in a frame which includes the base 21. The exit opening 2 of the housing 1 faces upwardly and is covered by a plate-like support or cover 22 for the body of a patient or for the bodies of several patients, depending on the dimensions of the exit opening 2. The material of the support 22 is selected in such a way that it transmits radiation in the desired wavelength band between 300 and 330 nm as well as that it can support one or more patients. The exposed (upper) side of the support is preferably concave so that it conforms to the curvature of the plane shown in FIG. 1. Moreover, such configuration of the upper side of the support 22 is more confortable to the patient utilizing the apparatus of FIG. 6. The inner side of the support 22 preferably abuts against and rests upon the front edges of the side walls of the reflectors 5 or 14. The apparatus of FIG. 6 insures that a substantial part of the body of a patient resting on the support 22 is necessarily located in the high-density radiation field. In other words, a patient resting on the support 22 is compelled to maintain a substantial part of his or her body in the region of high-density radiation field.

The radiation sources in the housing 1 can be assembled into several groups, and the support may comprise several sections each of which overlies a group of radiation sources.

Referring to FIG. 7, there is shown a composite apparatus which comprises two discrete apparatus, namely, a lower unit 23 and an upper unit 24. The lower unit 23 is analogous to the apparatus of FIG. 6, i.e., it comprises a plate-like support 27 which rests on the front edges of trough-shaped reflectors 14 in the exit opening above a battery of low-pressure mercury lamps 4. The housing 25 of the lower unit 23 has ground-contacting legs 26 forming part of a frame which may resemble the wedge-like member 21 of FIG. 6. The number of lamps 4 and reflectors 14 can be increased above or reduced to less than the number shown in the lower unit 23 of FIG. 7.

The upper unit 24 comprises a housing 28 for a battery of low-pressure mercury lamps 4 and trough-shaped reflectors 14. The exit opening of the housing 28 is covered by a glass plate 3. The entire unit 24 is suspended on one or more articulatable arms 29 which include sections 30 and 31. The section 31 carries the housing 28 and is pivoted or otherwise articulately connected to the section 30, and the latter is rigidly or adjustably (preferably articulately) connected to the wall W of the room in which the apparatus of FIG. 7 is installed. For example, the section 30 can swivel with respect to the wall W, and the section 31 can swivel with respect to the section 30 and housing 28. This enables the patient or an attendant (e.g., a nurse) to locate the upper unit 24 in an optimum position with respect to the body of a patient resting on the support 27 of the lower unit 23.

The arm 29 renders it possible to move the upper unit 24 out of the way when a patient desires to lie down on the support 27 or when a patient desires to get up upon completion of a treatment. Moreover, the upper unit 24 will be moved out of the way when the patient desires to be exposed solely to radiation which is furnished by the lower unit 23. When both units are in use, the pane 3 of the upper unit 24 is normally closely or immediately adjacent to the patient resting on the support 27.

It is clear that the upper and/or lower lamps 4 can be arrayed in a manner as shown in FIG. 1, i.e., so that the axes of the lamps are located in an arcuate plane whose convex side faces the space between the two units. This further increases the density of the respective radiation field. Such mounting of lamps is especially desirable in the upper unit 24 because it insures the establishment of a high-density radiation field at a desired distance from (in front of) the pane 3, i.e., at a distance which suffices to enable the patient resting on the support 27 to maintain the upper part of his or her body in the high-density radiation field of the upper unit 24. As a rule, the pane 3 will be held at a slight distance from the patient on the support 27.

An advantage of the apparatus of FIG. 7 is that the treatment can be completed within a short interval of time because the person resting on the support 27 is subjected to radiation from above as well as from below. Moreover, the support 27 insures that a large part of the body of a patient is invariably located in the high-density radiation field which is established by the lamps 4 and reflectors 14 of the lower unit 23.

FIG. 8 shows a further composite apparatus which includes three discrete apparatus, namely, a lower unit 32, an upper unit 33 and a lateral unit 34 between the upper and lower units so that the housings 35, 36, 37 of the three units resemble a U-shaped channel one side of which is open to afford access to or to permit a patient to leave the space between the units 32 and 33. The reference character 38 denotes one of the two end walls of the composite housing including the housings 35, 36, 37. Each unit includes a pane or plate 39 which does not intercept radiation in the wavelength band between approximately 300 and 330 nm. In the apparatus of FIG. 8, the three panes together form a U-shaped body which is assembled of narrow elongated strips 40. The width of each strip 40 may equal or approximate the width of a reflector 5 or 14 (not specifically shown in FIG. 8). However, it is equally within the purview of the invention to utilize strips each of which overlies only a fraction of a reflector or more than one reflector.

The apparatus of FIG. 8 can be installed in such a way that the housing 37 of the lateral unit 34 is adjacent and affixed to an upright wall (such as the wall W of FIG. 7) and that the underside of the housing 35 of the lower unit 32 is spaced apart from the floor so that a patient can readily sit down on the strips 40 of the lower unit prior to lying down on such strips in order to have his or her body exposed to radiation coming from three different sides.

The radiation issuing from the lamps of the lateral unit 34 contributes to the density of the radiation field which is established by the upper unit 33. The rays issuing from the front sides of reflectors in the lateral unit 34 are substantially normal to the rays which form the upper and lower radiation fields.

FIGS. 1, 6, 7 and 8 illustrate but a few of many apparatus which can be constructed and assembled in accordance with the present invention. For example, the upper and lower units 24 and 23 of FIG. 7 can be mounted on discrete carriers which allow for movements of the respective units in horizontal or substantially horizontal planes. This enables a patient to push the upper unit 24 away from a position of overlap with the lower unit 23 prior to lying down on the support 27 of the lower unit, and the upper unit 24 is thereupon returned to a position above the lower unit 23. The upright support for both carriers can be disposed at the one or the other narrower end of the lower unit 23. Moveover, the upper unit 24 of FIG. 7 (or a similar unit) can be combined with one or two lateral units to form therewith an inverted U-shaped channel which can be lowered toward or raised above the lower unit. A patient who rests on the lower unit is then exposed to radiation from all four sides. Still further, the apparatus of FIG. 7 may include one or two discrete lateral units which can be moved sideways toward or away from the respective sides of the lower unit 23. An upper unit and one or more lateral units can be assembled into a roof-shaped or cupola-like structure which is movable to and from an operative position above the lower unit.

The improved apparatus can be used for treatment of psoriasis or other skin diseases including acne, for development of D vitamins, for hardening of special types of polymers and/or as a sunlamp.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

What is claimed is:

1. Apparatus for selective treatment by ultraviolet radiation, especially for treatment of skin diseases including psoriasis, comprising a plurality of closely adjacent parallel elongated sources of ultraviolet radiation each including a low-pressure mercury lamp having a layer of luminous material, said sources being arranged to emit a continuous spectrum whose intensity is higly pronounced in the region between approximately 300 and 330 nm and decreases pronouncedly at the wavelength of approximately 330 nm; and filter means arranged to absorb radiation below approximately 295 nm, the transmissivity of said filter means increasing abruptly above 295 nm.

2. Apparatus as defined in claim 1, wherein the number of said radiation sources is between 5 and 20.

3. Apparatus as defined in claim 2, wherein said number is between 10 and 12.

4. Apparatus as defined in claim 1, wherein said radiation sources are cylinders and the spacing between neighboring sources at most equals the diameter of a cylinder.

5. Apparatus as defined in claim 1, wherein each of said radiation sources includes a tubular glass envelope, said envelopes constituting said filter means.

6. Apparatus as defined in claim 1, further comprising a plurality of substantially trough-shaped reflectors, one for each of said radiation sources and each surrounding the respective radiation source along an arc of at least 180 degrees.

7. Apparatus as defined in claim 6, further comprising a housing for said radiation sources and said reflectors, said housing having an exit opening for ultraviolet radiation and said reflectors having front sides facing said exit opening, each of said reflectors having two side walls including substantially parallel front portions disposed between the respective radiation source and said exit opening.

8. Apparatus as defined in claim 7, wherein each side wall of each of said reflectors defines with the respective radiation source a gap and each reflector further comprises a rear wall behind that portion of the respective radiation source which faces away from said exit opening, said rear walls having inner sides configurated to reflect radiation issuing from said portions of the respective sources into said gaps.

9. Apparatus as defined in claim 1, further comprising a housing for said radiation sources, said housing having an exit opening for ultraviolet radiation and said sources being closely adjacent to said exit opening.

10. Apparatus as defined in claim 1, further comprising a housing for said radiation sources, said housing having an exit opening for ultraviolet radiation and said radiation sources being substantially horizontal, and further comprising a substantially plate-like support in said opening, said support consisting of a material which transmits radiation in the wavelength band between approximately 300 and 330 nm.

11. Apparatus as defined in claim 10, wherein said radiation sources form several groups and said support includes a plurality of sections, one for each group of radiation sources.

12. Apparatus as defined in claim 10, wherein said support is disposed at a level above said radiation sources.

13. Apparatus as defined in claim 1, wherein said radiation sources are substantially horizontal and further comprising a housing for said sources, said housing having an exit opening above said radiation sources and a substantially plate-like support in said exit opening, and further comprising a second housing disposed above said first mentioned housing and having an exit opening facing said support, and a battery of substantially horizontal parallel radiation sources in said second housing above the respective exit opening.

14. Apparatus as defined in claim 13, further including reflectors for said radiation sources, at least two reflectors for the radiation sources in said second housing being arranged to direct radiation issuing from the respective sources downwardly through the respective exit opening so that the rays issuing from radiation sources associated with said two reflectors converge toward each other to form a high-density radiation field in a predetermined plane below the exit opening of said second housing.

15. Apparatus as defined in claim 13, further comprising a third housing laterally adjacent to said first mentioned housings and having an exit opening facing the space between said first mentioned housings, and a plurality of parallel elongated radiation sources in said third housing.

* * * * *